United States Patent
Valenti

(10) Patent No.: US 6,365,596 B1
(45) Date of Patent: Apr. 2, 2002

(54) ORAL PHARMACEUTICAL COMPOSITIONS CONTAINING BUPRENORPHIN

(75) Inventor: Mauro Valenti, Origgio (IT)

(73) Assignee: Farmaceutici Formenti S.p.A., Milan (IT)

( * ) Notice: Subject to any disclaimer, the term of this patent is extended or adjusted under 35 U.S.C. 154(b) by 0 days.

(21) Appl. No.: 09/807,216

(22) PCT Filed: Oct. 11, 1999

(86) PCT No.: PCT/EP99/07595

§ 371 Date: Apr. 17, 2001

§ 102(e) Date: Apr. 17, 2001

(87) PCT Pub. No.: WO00/23079

PCT Pub. Date: Apr. 27, 2000

(30) Foreign Application Priority Data

Oct. 16, 1998 (IT) .......................................... MI98A2222

(51) Int. Cl.$^7$ ................................................ A61K 31/44
(52) U.S. Cl. ....................................................... 514/282
(58) Field of Search ......................................... 514/282

(56) References Cited

FOREIGN PATENT DOCUMENTS

| EP | 0 180 303 | 5/1986 |
| WO | WO97/33566 | 9/1997 |

*Primary Examiner*—William R. A. Jarvis
(74) *Attorney, Agent, or Firm*—Nixon & Vanderhye

(57) ABSTRACT

An oral pharmaceutical composition containing buprenorphin or a pharmaceutically acceptable salt thereof as the active ingredient, characterized in that it contains a pharmaceutically acceptable antioxidant.

9 Claims, No Drawings

ORAL PHARMACEUTICAL COMPOSITIONS CONTAINING BUPRENORPHIN

This application is a 371 of PCT/EP99/07595, filed Oct. 11, 1999.

The present invention relates to oral pharmaceutical compositions, in particular to compositions containing buprenorphin as active ingredient. These compositions are particularly stable with respect to the commercially available products.

BACKGROUND OF THE INVENTION

Buprenorphin, namely 21-cyclopropyl-7α-(2-hydroxy-3,3-dimethyl-2butyl-)-6,14-endo-ethano-6,7,8,18-tetrahydroripavine, is a morphine alkaloid with analgesic properties. Its preparation is disclosed in U.S. Pat. No. 3,433,791, for a review see J. W. Lewis in Advan. Biochem. Psychopharmacol. Vol. 8, M. C. Braude et al. eds. (Raven Press, New York, 1974).

This analgesic is marketed under the trade marks TEMGESIC, BUPRENEX, LEPETAN.

Sublingual tablets containing buprenorphin as active ingredient, for example TEMGESIC 0.2 and 0.4 mg, show the presence of products from the degradation of the active ingredient.

DISCLOSURE OF THE INVENTION

It has now been found that the addition of pharmaceutically acceptable antioxidants gives oral pharmaceutical compositions, containing buprenorphin or a pharmaceutically acceptable salt thereof as active ingredient, a particularly good stability, decreasing the formation of the degradation products.

Advantageously, the oral pharmaceutical compositions according to the present invention are more stable than the presently available dosage forms of the state of the art, hence they have a longer shell-life.

Therefore, it is an object of the present invention an oral pharmaceutical composition containing buprenorphin or a pharmaceutically acceptable salt thereof as active ingredient characterised in that it contains a pharmaceutically acceptable antioxidant in addition to conventional vehicles and eccipients.

This and other objects of the present invention will be disclosed in detail, also by means of examples.

DETAILED DISCLOSURE OF THE INVENTION

Pharmaceutically acceptable antioxidants are well known to the person skilled in the art and are described in the technical literature forming the general common knowledge. A source of information, for example, can be found in "Remington's Pharmaceutical Sciences Handbook", Mack Pub. N.Y. U.S.A.

A first group of preferred antioxidants comprises ascorbic acid, its salts and esters, Vitamin E, tocopherol and its salts, sodium metabisulphite, butylated hydroxyanisole (BHA), butylated hydroxytoluene (BHT).

A more preferred group of antioxidants comprises ascorbic acid, sodium metabisulphite, Vitamin E, alpha-lipoic acid.

The most preferred antioxidant is ascorbic acid.

The molar ratio between the antioxidant and buprenorphin is at least 1:1, more preferably 3:1.

The commercial formulations contain magnesium ions due to the presence of magnesium stearate, a well-known lubricant.

It has surprisingly been found that significantly better results are achieved if the presence of magnesium ion is avoided in the formulation of the present invention. Therefore, a further object of the present invention is an oral formulation containing buprenorphin or a pharmaceutically acceptable salt thereof as active ingredient characterised in that it further contains a pharmaceutically acceptable antioxidant and in that the magnesium ion is absent.

In a first embodiment of this further aspect of the invention, magnesium stearate is substituted by another lubricant. Hydrogenated castor oil is a preferred example.

It has further surprisingly been found that significant results are also achieved if the presence of magnesium ion is avoided and the buffer system is changed in the formulation of the present invention. Therefore, a further object of the present invention is an oral formulation containing buprenorphin or a pharmaceutically acceptable salt thereof as active ingredient characterised in that it further contains a pharmaceutically acceptable antioxidant, in that the magnesium ion is absent and in that the buffer system differs from that of the commercial formulations.

In a preferred embodiment of this further aspect of the invention, glycine/hydrochloric acid is the buffer system.

The formulations obtained according to this further aspects of the present invention, are fully satisfactory in view of the stability of the active ingredient, but have a poor external aspect, so that the consumers could not accept them.

While searching to improve the stability of the oral formulation, by reducing the amount of degradation products, and maintaining a good external aspect it has surprisingly been found that the elimination of polyvinylpyrrolidone, even keeping magnesium stearate as lubricant, and without changing the buffer system, gives very good results. Therefore, a further aspect of the present invention is an oral pharmaceutical composition containing buprenorphin or a pharmaceutically acceptable salt thereof as active ingredient characterised in that it further contains a pharmaceutically acceptable antioxidant and in that it does not contain polyvinylpyrrolidone.

The present invention applies to oral dosage forms. Oral dosage forms are conventionally known in the art, and no particular disclosure is herein needed, since they can be prepared by resorting to general common knowledge as provided by textbooks, manuals and other technical literature, which are normally available.

Examples of oral dosage forms are pills, capsules, tablets, powders, solutions, suspensions and the like. In a preferred embodiment of this invention, oral compositions are in the form of sublingual tablets.

Commercial batches of TEMGESIC having the same quali-quantitative composition were replicated (hereinafter referred to as "FRT") and tested for stability together with a batch of TEMGESIC as available on the market.

Stability protocols were designed as outlined in Table 1 below:

TABLE 1

STABILITY PROTOCOLS
Batch FRT 10097 0.4 mg
Batch FRT 16097 0.2 mg
Batch Temgesic T19501 0.2 mg
1. IN GLASS VIALS

| Temperature | 7 days | 15 days | 30 days |
|---|---|---|---|
| 25° C. + 60% R.H. | | | X |
| 30° C. + 70% R.H. | | X | X |
| 40° C. + 75% R.H. | X | X | X |
| 50° C. | X | X | X |

RH = Relative humidity

The studies were directed at the determination of the titre of the active ingredient and of the related degradation products.

TABLE 2 shows the results.

TABLE 2

Stability studies in glass vials.

| | Batch 10097 0.4 mg | | Batch 16097 0.2 mg | | Temgesic Batch T19501 0.2 mg | |
|---|---|---|---|---|---|---|
| days | Titre in Buprenorphin | Total degradation products | Titre in Buprenorphin | Total degradation products | Titre in Buprenorphin | Total degradation products |
| Temperature 25° C. + 60% R.H. | | | | | | |
| 0 | 99.29% | 1.19% | 99.40% | 1.84% | 96.10% | 2.97% |
| 30 | 96.82% | 7.22% | 97.8% | 5.62% | 90.45% | 7.49% |
| Temperature 30° C. + 70% R.H. | | | | | | |
| 0 | 99.29% | 1.19% | 99.40% | 1.84% | 96.10% | 2.97% |
| 15 | 94.65% | 8.05% | 97.57% | 5.71% | 91.16% | 7.97% |
| 30 | 94.62% | 9.42% | 97.80% | 5.62% | 88.16% | 10.51% |
| Temperature 40° C. + 75% R.H. | | | | | | |
| 0 | 99.29% | 1.19% | 99.40% | 1.84% | 96.10% | 2.97% |
| 7 | 98.78% | 2.31% | 97.78% | 3.30% | 92.92% | 6.10% |
| 15 | 95.96% | 2.82% | 94.95% | 4.33% | 87.42% | 8.25% |
| 30 | 98.28% | 3.85% | 96.16% | 5.43% | 86.43% | 9.06% |
| Temperature 50° C. | | | | | | |
| 0 | 99.29% | 1.19% | 99.40% | 1.84% | 96.10% | 2.97% |
| 7 | 89.66% | 10.47% | 93.54% | 7.43% | 85.59% | 11.44% |
| 15 | 89.42% | 9.97% | 95.23% | 6.25% | 84.71% | 10.56% |
| 30 | 88.88% | 11.31% | 96.52% | 6.69% | 77.23% | 15.15% |

Three batches of buprenorphin tablets were prepared according to the present invention, each batch containing a different pharmaceutically acceptable antioxidant. The compositions of the batches are shown in Table 3 below.

The molar ratio antioxidant/buprenorphin is 1/1.

TABLE 3

FORMULATIONS

| INGREDIENT NAME | Example 1 Vitamin C Batch 23038 | Example 2 Sodium Metabisulphite Batch 24038 | Example 3 Vitamin E Batch 25038 |
|---|---|---|---|
| Buprenorphin hydrochloride | 0.216 mg | 0.216 mg | 0.216 mg |
| Equivalent to Buprenorphin | 0.200 mg | 0.200 mg | 0.200 mg |
| Antioxidant | 0.151 mg | 0.163 mg | 0.405 mg |
| Lactose | 29.690 mg | 29.678 mg | 29.436 mg |
| Maize starch | 9.000 mg | 9.000 mg | 9.000 mg |
| Mannitol | 18.000 mg | 18.000 mg | 18.000 mg |
| Polyvinylpyrrolidone | 1.200 mg | 1.200 mg | 1.200 mg |
| Anhydrous Citric Acid | 0.888 mg | 0.888 mg | 0.888 mg |
| Sodium Citrate 2H$_2$O | 0.405 mg | 0.405 mg | 0.405 mg |
| Magnesium Stearate | 0.450 mg | 0.450 mg | 0.450 mg |

The batches were tested for stability according to the experimental protocol shown in Table 4 below.

TABLE 4

STABILITY PROTOCOLS
(In glass vials)
1.

| Temperature | 0.5 Months | 1. Month | 2.0 Months | 3.0 Months |
|---|---|---|---|---|
| 25° C. + 60% R.H. | | X | X | X |
| 40° C. + 75% R.H. | X | X | X | X |
| 50° C. | X | | X | X |
| 80° C. | X | X | | |

The results are shown in tables 5–7 below.

TABLE 5

Buprenorphin tablets 0.2 mg - Batch 23038 with Vit. C 1/1

| Conditions | Time | Titre in Buprenorphin | Total Degradation products |
|---|---|---|---|
| | Initial | 101.00% | 0.10% |
| 25° C. + 60% R.H. | 1 month | 100.63% | 0.11% |
| 25° C. + 60% R.H. | 2 months | 100.90% | 0.57% |
| 25° C. + 60% R.H. | 3 months | 99.21% | 0.48% |
| 40° C. + 75% R.H. | 0.5 months | 102.54% | 0.35% |
| 40° C. + 75% R.H. | 1 month | 100.15% | 0.57% |
| 40° C. + 75% R.H. | 2 months | 101.06% | 0.73% |
| 40° C. + 75% R.H. | 3 months | 98.68% | 0.78% |
| 50° C. | 0.5 months | 102.59% | 0.69% |
| 50° C. | 2 months | 102.23% | 0.83% |
| 50° C. | 3 months | 102.54% | 1.12% |
| 80° C. | 0.5 months | 97.73% | 2.44% |
| 80° C. | 1 month | 93.34% | 3.76% |

TABLE 6

Buprenorphin tablets 0.2 mg - Batch 24038 with Metabis. 1/1

| Conditions | Time | Titre in Buprenorphin | Total Degradation products |
|---|---|---|---|
| | Initial | 100.43% | 0.11% |
| 25° C. + 60% R.H. | 1 month | 99.60% | 0.78% |
| 25° C. + 60% R.H. | 2 months | 100.91% | 1.55% |
| 25° C. + 60% R.H. | 3 months | 98.06% | 2.00% |
| 40° C. + 75% R.H. | 0.5 months | 101.10% | 1.13% |
| 40° C. + 75% R.H. | 1 month | 99.79% | 3.12% |
| 40° C. + 75% R.H. | 2 months | 99.78% | 3.05% |
| 40° C. + 75% R.H. | 3 months | 98.41% | 3.83% |
| 50° C. | 0.5 months | 101.42% | 1.47% |
| 50° C. | 2 months | 99.06% | 2.77% |

TABLE 6-continued

Buprenorphin tablets 0.2 mg - Batch 24038 with Metabis. 1/1

| Conditions | Time | Titre in Buprenorphin | Total Degradation products |
|---|---|---|---|
| 50° C. | 3 months | 99.62% | 2.83% |
| 80° C. | 0.5 months | 93.48% | 4.61% |
| 80° C. | 1 month | 90.54% | 11.28% |

TABLE 7

Buprenorphin tablets 0.2 mg - Batch 25038 with Vit. E 1/1

| Conditions | Time | Titre in Buprenorphin | Total Degradation products |
|---|---|---|---|
| | Initial | 98.83% | 0.09% |
| 25° C. + 60% R.H. | 1 month | 100.14% | 0.64% |
| 25° C. + 60% R.H. | 2 months | 98.86% | 1.85% |
| 25° C. + 60% R.H. | 3 months | 98.90% | 2.89% |
| 40° C. + 75% R.H. | 0.5 months | 100.20% | 1.20% |
| 40° C. + 75% R.H. | 1 month | 98.35% | 1.74% |
| 40° C. + 75% R.H. | 2 months | 102.64% | 4.66% |
| 40° C. + 75% R.H. | 3 months | 95.40% | 5.81% |
| 50° C. | 0.5 months | 98.41% | 2.64% |
| 50° C. | 2 months | 95.78% | 5.35% |
| 50° C. | 3 months | 95.48% | 5.34% |
| 80° C. | 0.5 months | 94.60% | 4.18% |
| 80° C. | 1 month | 89.49% | 4.81% |

The compositions according to the present invention are more stable than those commercially available and those replicated by Formenti.

It shall be noted that ascorbic acid gives very good results. The total amount of degradation products is by far lower than the one found in commercial products, even in the worst conditions of experimental protocol. Sodium metabisulphite and Vitamin E give the same results.

Another embodiment of the present invention is disclosed in the following. Three batches were prepared according to the experimental design of Table 8 below. Ascorbic acid is used in a molar ratio of 3/1 with respect to the active ingredient. In a second batch, magnesium ion is eliminated and an alternative lubricant is used. In a third batch, together the alternative lubricant, also a different buffer system is used.

TABLE 8

FORMULATIONS

| INGREDIENTS | Example 4 Batch 08048 | Example 5 Batch 09048 | Example 6 Batch 10048 |
|---|---|---|---|
| Buprenorphin Hydrochloride | 0.216 mg | 0.216 mg | 0.216 mg |
| Equivalent to Buprenorphin | 0.200 mg | 0.200 mg | 0.200 mg |
| Vitamin C | 0.453 mg | 0.453 mg | 0.453 mg |
| Lactose | 29.388 mg | 29.238 mg | 29.379 mg |
| Maize starch | 9.000 mg | 9.000 mg | 9.000 mg |
| Mannitol | 18.000 mg | 18.000 mg | 18.000 mg |
| Polyvinylpyrrolidone | 1.200 mg | 1.200 mg | 1.200 mg |
| Anhydrous Citric Acid | 0.888 mg | 0.888 mg | — |
| Sodium Citrate. 2H$_2$O | 0.405 mg | 0.405 mg | — |
| Magnesium Stearate | 0.450 mg | — | — |
| Hydrogenated castor oil | — | 0.600 mg | 0.600 mg |
| Glycine/Hydrochloric acid | — | — | 0.955 mg |
| Hydrochloric Acid to pH 3.3 | — | — 2 | ml |

Stability protocols are the same as the former tests. The results are shown in tables 9–11 below.

TABLE 9

Buprenorphin tablets 0.2 mg - Batch 25038 with Vit. E 1/1

| Conditions | Time | Titre in Buprenorphin | Total Degradation Products |
|---|---|---|---|
| | Initial | 100.93% | 0.16% |
| 25° C. + 60% R.H. | 1 month | 99.30% | 0.31% |
| 25° C. + 60% R.H. | 2 months | 103.23% | 0.47% |
| 25° C. + 60% R.H. | 3 months | 102,17% | 0.47% |
| 40° C. + 75% R.H. | 0.5 months | 102.98% | 0.21% |
| 40° C. + 75% R.H. | 1 month | 103,35% | 0.51% |
| 40° C. + 75% R.H. | 2 months | 102.52% | 0.52% |
| 40° C. + 75% R.H. | 3 months | 103.80% | 0.52% |
| 50° C. | 0.5 months | 103.10% | 0.21% |
| 50° C. | 2 months | 103.41% | 0.54% |
| 50° C. | 3 months | 100.74% | 0.66% |
| 80° C. | 0.5 months | 97.93% | 2.01% |
| 80° C. | 1 month | 92.02% | 4.63% |

TABLE 10

Buprenorphin tablets 0.2 mg - Batch 09048 with Vit. C 3/1

| Conditions | Time | Titre in Buprenorphin | Total degradation products |
|---|---|---|---|
| | Initial | 100.81% | 0.16% |
| 25° C. + 60% R.H. | 1 month | 101.35% | 0.40% |
| 25° C. + 60% R.H. | 2 months | 101.89% | 0.32% |
| 25° C. + 60% R.H. | 3 months | 104.38% | 0.42% |
| 40° C. + 75% R.H. | 0.5 months | 102.73% | 0.16% |
| 40° C. + 75% R.H. | 1 month | 101.22% | 0.32% |
| 40° C. + 75% R.H. | 2 months | 102.43% | 0.32% |
| 40° C. + 75% R.H. | 3 months | 103.45% | 0.44% |
| 50° C. | 0.5 months | 101.62% | 0.16% |
| 50° C. | 1 month | 100.86% | 0.64% |
| 50° C. | 2 months | 101.88% | 0.49% |
| 50° C. | 3 months | 103.38% | 0.56% |
| 80° C. | 0.5 months | 98.58% | 1.74% |
| 80° C. | 1 month | 92.72% | 4.70% |

TABLE 11

Buprenorphin tablets 0.2 mg - Batch 10048 with Vit. C 1/1 Glycine/hydrochloride acid and hydrogenated castor oil

| Conditions | Time | Titre in Buprenorphin | Total Degradation products |
|---|---|---|---|
| | Initial | 101.21% | 0.15% |
| 25° C. + 60% R.H. | 1 month | 101.39% | 0.49% |
| 25° C. + 60% R.H. | 2 months | 101.22% | 0.30% |
| 25° C. + 60% R.H. | 3 months | 101.36% | 0.29% |
| 40° C. + 75% R.H. | 0.5 months | 103.27% | 0.18% |

TABLE 11-continued

Buprenorphin tablets 0.2 mg - Batch 10048 with Vit. C 1/1
Glycine/hydrochloride acid and hydrogenated castor oil

| Conditions | Time | Titre in Buprenorphin | Total Degradation products |
|---|---|---|---|
| 40° C. + 75% R.H. | 1 month | 100.44% | 0.90% |
| 40° C. + 75% R.H. | 2 months | 101.72% | 0.32% |
| 40° C. + 75% R.H. | 3 months | 104.68% | 0.29% |
| 50° C. | 0.5 months | 101.96% | 0.25% |
| 50° C. | 1 month | 99.20% | 0.51% |
| 50° C. | 2 months | 101.78% | 0.41% |
| 50° C. | 3 months | 100.01% | 0.54% |
| 80° C. | 0.5 months | 100.00% | 1.41% |
| 80° C. | 1 month | 94.62% | 5.25% |

The compositions according to this embodiment of the present invention have the same stability of those of the first embodiment at r.t., but the amount of degradation products is decreased. Advantageously, this second embodiment gives a higher stability at more severe conditions.

It shall be noted that the elimination of magnesium ions still improves stability. Changing buffer system also confirms the trend to good results.

Another embodiment of the present invention comprises the elimination of polyvinylpyrrolidone from the formulation.

Buprenorphin sublingual tablets were prepared according to the following composition:

| INGREDIENT | Example 7 Buprenorphin 0.2 mg | Example 8 Buprenorphin 0.4 mg |
|---|---|---|
| Buprenorphin Hydrochloride | 0.216 mg | 0.432 mg |
| Equivalent to Buprenorphin | 0.200 mg | 0.400 mg |
| Vitamin C | 0.453 mg | 0.906 mg |
| Lactose | 30.588 mg | 29.919 mg |
| Maize starch | 9.000 mg | 9.000 mg |
| Mannitol | 18.000 mg | 18.000 mg |
| Citric acid hydrochloride | 0.888 mg | 0.888 mg |
| Sodium Citrate .2H$_2$O | 0.405 mg | 0.405 mg |
| Magnesium Stearate | 0.450 mg | 0.450 mg |

The tablets comply with the analytical requirements.

TABLE 12

| Assay | References | Limits | Results Buprenorphin tablets 0,2 mg | Results Buprenorphin tablets 0,4 mg |
|---|---|---|---|---|
| Appearance | | Must comply | Complies | Complies |
| Buprenorphin identification | | Must comply | Positive | Positive |
| Average weight | Eur. Ph., III ed. | 60 mg/tablet | 59.58 mg | 59.85 mg |
| Weight uniformity | Eur. Ph., III ed. | Must comply | Complies | Complies |
| Content uniformity | Eur. Ph., III ed. | Must comply | Complies | Complies |
| Water | Eur. Ph., III ed. | ≦5.0% | 3.87% | 350% |
| Disintegration Test | Eur. Ph., III ed. | ≦5 minutes | ≦1 minutes | ≦1 minutes |
| Dissolution Test | Eur. Ph., III ed. | | | |
| - After 2 minutes | | ≧60.0% | 92.2% | 93,2% |
| - After 4 minutes | | ≧80.0% | 94.0% | 95,4% |
| Degradation products | | ≦2.0% total | ≦0.1% | ≦0.1% |
| Titre | | 95.0–105.0% | 100.62% | 100.62% |

What is claimed is:

1. An oral pharmaceutical composition containing buprenorphin or a pharmaceutically acceptable salt thereof as active ingredient characterised in that it further contains a pharmaceutically acceptable antioxidant in a molar ratio between said antioxidant and buprenorphin ranging from 1:1 to 3:1.

2. An oral pharmaceutical composition according to claim 1, wherein said antioxidant is selected from the group consisting of: ascorbic acid, its salts and esters, Vitamin E, tocopherol and its salts, sodium metabisulphite, butylated hydroxyanisole (BHA), butylated hydroxytoluene (BHT), alpha-lipoic acid.

3. An oral pharmaceutical composition according to claim 2, wherein said antioxidant is selected from the group consisting of: ascorbic acid, its salts and esters, Vitamin E, sodium metabisulphite.

4. An oral pharmaceutical composition according to claim 3, wherein said antioxidant is ascorbic acid, its salts and esters.

5. An oral pharmaceutical composition according to any one of claims 1–4, wherein the magnesium ion is absent.

6. An oral pharmaceutical composition according to claim 5, wherein hydrogenated castor oil is the lubricant.

7. An oral pharmaceutical composition according to claim 1, wherein glycine/hydrochloric acid is the buffer system.

8. An oral pharmaceutical composition according to claim 1, wherein polyvinylpyrrolidone is absent.

9. An oral pharmaceutical composition according to claim 1 in the form of a sublingual tablet.

* * * * *